United States Patent [19]

Nobile

[11] 4,265,823

[45] May 5, 1981

[54] AUROTHIOSTEROIDS

[75] Inventor: Arthur Nobile, West Caldwell, N.J.

[73] Assignee: Robert E. Kosinski, Rye, N.Y.; a part interest

[21] Appl. No.: 129,069

[22] Filed: Mar. 10, 1980

Related U.S. Application Data

[63] Continuation of Ser. No. 810, Jan. 4, 1979, abandoned, which is a continuation of Ser. No. 847,011, Oct. 31, 1977, abandoned, which is a continuation-in-part of Ser. No. 663,160, Mar. 2, 1976, abandoned.

[51] Int. Cl.³ .................................................. C07J 5/00
[52] U.S. Cl. ............................ 260/397.4; 260/397.45; 260/397.1; 260/397.5; 424/238; 424/243
[58] Field of Search ............... 260/397.4, 397.5, 397.1, 260/397.45

[56] References Cited

U.S. PATENT DOCUMENTS

| | | | |
|---|---|---|---|
| 3,944,576 | 3/1976 | Van den Broek et al. | 260/397.4 |
| 4,093,721 | 6/1978 | Phillipps et al. | 260/397.1 |

OTHER PUBLICATIONS

Oliveto et al., "JACS", (1958), p. 4431.

*Primary Examiner*—Elbert L. Roberts

[57] ABSTRACT

A novel class of gold-steroid compounds are produced by addition of aurothio substituents at various positions in steroids, particularly the 3-keto androstane, estrane and pregnane series unsaturated in the A ring. They possess potent anti-inflammatory properties and manifest unique therapeutic effects heretofore unavailable through conventional therapy.

8 Claims, No Drawings

AUROTHIOSTEROIDS

This is a continuation of application Ser. No. 000,810, filed Jan. 4, 1979, which is a continuation of Ser. No. 847,011 filed Oct. 31, 1977, which is a continuation-in-part of Ser. No. 663,160 filed March 2, 1976, all now abandoned.

The invention relates to a new class of gold-steroid compounds, particularly aurothio derivatives of the 3-keto androstane, estrane and pregnane series unsaturated in ring A. The aurothio group moiety is preferably organic, e.g., aurothiomalate and aurothiogluconate esters, but may also be inorganic, e.g., gold thiosulfate and incorporated at other side positions of the steroid molecule or in nuclear configurations.

It is an object of this invention to provide a new class of heretofore unknown compounds known as aurothiosteroids. It is an additional object of this invention to provide a process for the synthesis of aurothiosteroids.

A number of steroids of the corticoid series such as for example prednisone, prednisolone, triamcinolone and dexamethasone are recognized as important therapeutic anti-inflammatory agents. Gold salt therapy has also been long known to be a therapeutically effective anti-inflammatory. Yet both therapies have suffered from numerous dosage-related side effects. It is an object of this invention to provide novel compounds which combine both corticosteroid and gold salt therapy effects while reducing the effective dosage of each agent.

The use of corticosteroid therapy for inflammatory diseases is well known. An example of compounds used in such therapy may be found in U.S. Pat. Nos. 2,798,118, 2,897,218 and 3,134,718.

The use of gold salts in the treatment of inflammatory diseases has been well known since the 1920's. Examples of such therapy may be found in:

1. Forestier J: L'aurotherapie dans les rhumatismes chroniques. Bull Soc Med Hop Paris 53:323, 1929
2. Empire Rheumatism Council: Gold Therapy in Rheumatoid Arthritis. Ann Rheum Dis 19:95, 1960
3. Empire Rheumatism Council: Gold Therapy in Rheumatoid Arthritis. Ann Rheum Dis 20:315, 1961

Aurothiocorticosteroids produced in accordance with the present invention possess potent anti-inflammatory activity and are highly effacacious for use in the treatment of arthritis and many other diseases, including endocrine disorders, rheumatic disorders, collagen diseases, dermatologic diseases, allergic states, opthalmic diseases, respiratory diseases, hematologic disorders, neoplastic diseases, edematous states, tuberculous meningitis and autoimmune diseases. Furthermore they manifest clinical advantages not heretofore obtainable, including providing, in a single composition, the clinical advantages of the aurothio series of anti-inflammatory agents, such as sodium aurothiomalate together with the clinical advantages of the pregnadiene compounds, such as prednisolone. These new chemotherapeutic compositions open up an entirely new mode of therapy for the treatment of anti-inflammatory conditions, particularly when complicated with the other diseases enumerated above.

Gold salts are also known to have antimicrobial activity. See Chemotherapy of Tuberculosis by Holger Mollgaard (1924).

One novel class of aurothiocorticoids of my invention may be generally illustrated by the following formula:

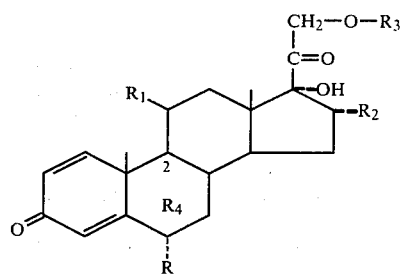

wherein R is hydrogen, alkyl or halide, $R_1$ is hydroxy or oxo, $R_2$ is hydrogen, hydroxy or alkyl, $R_3$ is an aurothio moiety, e.g., aurothiomalate and $R_4$ is hydrogen or halide.

Preferred compositions include 21-aurothio substituted, e.g., 21-aurothiomalate ester of prednisone, prednisolone, methyl prednisolone, dexamethasone, betamethasone, paramethasone, triamcinolone and beclomethasone.

The alpha configuration of the 21-aurothiomalate, which may also be in beta form, of delta-1,4-pregnadiene-17-alpha,11-beta diol, 3,20-dione is shown by the structural formula

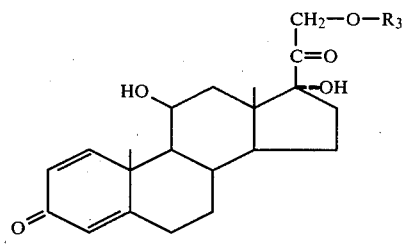

wherein $R_3$ is

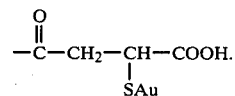

In the general structure representing both alpha and beta forms, $R_3$ is

Other aurothio organic moieties may be incorporated in the corticoid molecule, e.g., aurothiogluconate as well as inorganic moieties, e.g., aurothiosulfate. The aurothio moiety may also be incorporated by addition at other side chain positions, e.g., the 17 position as illustrated in the general formula above or attached in nuclear configuration for example at carbon 7.

PREPARATION OF AUROTHIOMALIC ACID ANHYDRIDE

EXAMPLE 1

500 mg of sodium aurothiomalate are dissolved in 1.5 ml of water at room temperature and the solution is acidified to a pH of 3.5–4.0 by the addition of a few drops of concentrated hydrochloric acid. The colorless aqueous solution so obtained is then concentrated to dryness at 35°–40° C. by vacuum distillation. To the white crystalline mixture, comprising aurothiomalic acid and sodium chloride is added 3 ml of dimethylformamide and 2 ml of trifluoroacetic anhydride. The mixture so formed is stirred for 16 hours at room temperature and filtered to remove inorganic salts. Excess trifluoroacetic anhydride and trifluoroacetic acid are then removed by vacuum distillation below 40° C. The liquid residue containing aurothiomalic acid anhydride and dimethylformamide may then be used directly for the esterification of hydroxyl moieties of the steroid molecule.

EXAMPLE 2

5 mg of sodium aurothiomalate is dissolved in 15 cc of water and the solution acidified with 10% hydrochloric acid to a pH of 4. The aqueous solution which contains aurothiomalic acid and sodium chloride is subjected to lyophilization (freeze drying) to remove the water. The freeze-dried residue is suspended in 15 cc acetic anhydride and heated under reflux for four hours. At the end of this period, excess anhydride and acetic acid are removed by evaporation under vacuum. The residue so obtained is crystallized from ether to give the aurothiomalic anhydride.

PREPARATION OF THE IMIDAZOLE OF AUROTHIOMALIC ACID

EXAMPLE 3

Approximately 346 mg of aurothiomalic acid is prepared from 390 mg of the di-sodium salt in the manner described in Example 1. The crystalline mixture comprising aurothiomalic acid and sodium chloride is then treated with 2 ml of dimethylsulfoxide and 178.4 mg of n,n'-carbonyldiimidazole. This mixture so formed is stirred for 3 hours in an inert atmosphere and filtered to remove inorganic salts. The filtrate now containing approximately 415 mg of the imidazole of aurothiomalic acid may be used directly without further isolation for the esterification of hydroxyl moieties of the steroid molecule.

PREPARATION OF PREDNISOLONE 21-AUROTHIOMALATE

EXAMPLE 4

To 100 mg of prednisolone dissolved in 0.5 ml of pyridine is added 1.5 ml of a solution containing dimethylformamide and 300 mg of aurothiomalic acid anhydride. This mixture is heated to about 70° C. for 1 hour and then allowed to remain at ambient temperature for 24 hours. Dilution of the mixture with 20 ml of 10% aqueous hydrochloric (or sulfuric) acid is followed by an extraction with chloroform to yield a mixture containing the desired product as a major component. The placement of the chloroform solution on a column of silica gel followed by elution with toluene-methanol 1:1 (v/v), separates the desired 21-ester from the other components. Crystallization from chloroform-ether then yields prednisolone-21-aurothiomalate as a crystalline product.

EXAMPLE 5

To a mixture comprising 100.2 mg of prednisolone, 4 ml of tetrahydrofuron and 2 ml of a solution containing 415 mg of the imidazole of aurothiomalic acid dissolved in dimethylsulfoxide is added 6 mg of sodium methoxide. The reaction mixture is stirred for approximately 1 hour in a dry, inert atmosphere.

Removal of tetrahydrofuron by vacuum distillation at or below 35° C. followed by dilution of the residue with ice water affords a solid mixture containing the desired product as a major component. A chloroform solution of the crude mixture is then placed on a column of silica gel. Elution of the column with toluene-methanol 9:1 (v/v) separates the 21-aurothiomalate from undesirable components. Purification of the desired product is accomplished by recrystallization with chloroform-ether.

EXAMPLE 6

1 g of prednisolone is dissolved in 5 cc of pyridine and 1 g of aurothiomalic anhydride is added. The mixture is heated to about 70° C. until a solution is obtained and then allowed to stand at room temperature for at least 24 hours. The excess pyridine is evaporated under a stream of nitrogen and the residue so obtained is crystallized from chloroform-ether to give 21-aurothiomalate of prednisolone.

Dosage of these aurothiocorticoids will be in a sufficient quantity to elecit a positive therapeutic response and are administered by conventional means, i.e., orally, intramuscularly, intra-articularly, subcutaneously or topically in a suitable liquid or solid media. Dosage forms of the compounds of my invention are formulated in liquid or solid non-toxic carriers. Examples of oral dosage forms are tablets, capsules, liquid suspensions or solutions. For parental dosage forms, a sterile diluent is necessary. When the active ingredients are for topical use they can be prepared as an ointment, lotion, gel or cream. For eye, ear or nose indications the compounds can be formulated in the form of drops or ointment.

Tablets for Oral Indications

| 1. | Aurothioprednisone | 5.0 mg |
|---|---|---|
| 2. | Lactose | 83.0 |
| 3. | Gelatin | 1.2 |
| 4. | Starch | 9.5 |
| 5. | Calcium stearate | 0.46 |

Other strengths of the active compounds of my invention can be formulated varying from 0.5 mg to 50.0 mg/tablet, or higher depending on the severity of the disease. In addition, one or more other active compounds may be formulated in the tablet such as antibiotics, sulfas, aspirin or vitamins.

Ointment for Topical Indications

| 1. | Aurothio-3-keto steroid | 5.0 mg/g |
|---|---|---|
| 2. | Methyl paraben | 1.7 |
| 3. | Propyl paraben | 0.3 |
| 4. | Liquid petrolatum | 120.0 |
| 5. | Lanolum | 200.0 |
| 6. | White petrolatum | 668.0 |

Injectable Aqueous Suspension (Intra-articular)

| 1. | Aurothio-3-keto steroid | 0.5% |
|---|---|---|
| 2. | Sodium chloride | 0.9 |
| 3. | Sodiumcarboxymethylcellulose | 0.4 |
| 4. | Polyoxyethylenesorbitanmono- | |

|   |         |       |
|---|---------|-------|
|   | oleate  | 0.4   |
| 5.| Benzyl alcohol | 0.9 |
| 6.| Water q.s. | 100.0 |

Injectable Oil Suspension (Intramuscular-Subcutaneous)

| 1. | Aurothio-3-keto steroid | 50.0 mg/ml |
|---|---|---|
| 2. | Aluminum monostearate | 20.0 |
| 3. | Propyl paraben | 1.0 |
| 4. | Sesame Oil To make | 1.0 ml |

Aqueous Suspension (Intramuscular-Subcutaneous and Opthalmic)

| 1. | Aurothio-3-keto steroid-sterile | 50.0 mg/ml |
|---|---|---|
| 2. | KH$_2$PO$_4$ | 6.0 |
| 3. | NA$_2$HPO$_4$ | 12.0 |
| 4. | Tween-80-Atlas | 0.4 |
| 5. | Span-20-Atlas | 0.4 |
| 6. | Thimerosal NF Lilly | 0.1 |
| 7. | Water To make | 1.0 ml |

Cream for Topical Indications

| 1. | Aurothio-3-keto steroid | 5.0 mg/g |
|---|---|---|
| 2. | Zn stearate | 60.9 |
| 3. | Carbowax (6000) | 122.0 |
| 4. | Carbowax (1500) | 421.0 |
| 5. | Polypropylene glycol USP | 345.0 |
| 6. | Distilled water | 45.0 |

Administration of the aurothiosteroids can be expected to result in a reduction of adverse side effects, such as blood dyscrasias, bone marrow depression and others due to a reduced dosage of the aurothio moiety and Cushing's Syndrome, electrolyte imbalance, osteoporosis, psychiatric, gastrointestinal bleeding, infection susceptability and others, as a result of the reduced strength of the corticoid moiety of my invention.

Administration of the aurothiosteroids have the advantage of imparting immediate clincal relief as compared with a dose response of from 10-20 weeks or beyond—if at all—with usual gold salt treatment.

Administration of aurothiosteroids have the added advantage that during severe inflammatory episodes, increasing the dose of plain corticoids may impart no additional anti-inflammatory response while, due to the presence of the aurothio moiety of my invention, anti-inflammatory response is expected.

Administration of the novel compounds of my invention have the advantage of providing anti-inflammatory relief during corticoid relapse, which may occur when an arthritic is on plain corticoid.

Administration of aurothiosteroids can be recommended for both mild to severe inflammatory conditions, since sodium aurothiomalate is indicated for mild inflammatory conditions and corticoids for usually severe states.

Administration of aurothiosteroids is a convenient form of therapy for inflammatory conditions for patients who have responded to sodiumaurothiomalate or corticoid in equivalent doses.

The advantages of administration of aurothiosteroids for anti-inflammatory effect encourage patients to continue medication for reasons of efficacy, reduced side effects and convenience to patients for both mild and severe inflammations.

As with all drugs, dose requirements may vary depending on the specific disease, severity, individual patient response, drug solubility, route of administration and formula vehicle. The products of my invention provide a dosage flexibility heretofore unknown for anti-inflammatory diseases. It can be expected that prednisoloneaurothiomalate be the aurothiocorticoid of choice in which to initiate and maintain therapy. If patient requirements for more corticoid and less aurothiomalate are demanded for clinical response, then dexamethasoneaurothiomalate can be administered. If the requirement for more autothiomalate and less corticoid are in demand hydrocortisoneaurothiomalate can be administered.

Initial and maintenance dose of prednisoloneaurothiomalate is about 50 mg/week until optical clinical response can be ascertained. If necessary, dose can be altered on either side of 50 mg. If patient is to be switched from prednisolone acetate to prednisoloneaurothiomalate, the prednisolone acetate can be referenced as a starting dose.

Dose Recommendations of Aurothiocorticoids

| Controls vs. Aurothiocorticoid | Initial Therapy | Maintenance Therapy |
|---|---|---|
| Aurothiomalate* | 25 mg/week | 50 mg/week |
| Hydrosortisone** | 50-100 mg | 50-100 mg |
| Hydrocortisone-aurothio | 50 mg | 50-100 mg |
| Prednisolone** | 25-50 mg | 25-50 mg |
| Prednisoloneaurothio | 50 mg | 50 mg |
| Dexamethasone** | 4-20 mg | 4-20 mg |
| Dexamethasoneaurothio | 4 mg | 4-8 mg |

*Sodium
**Acetate

Dose Recommendations of
Prednisoloneaurothiomalate

Initial therapy with prednisoloneaurothiomalate can begin at 50 mg until clinical response can be ascertained. If necessary, dose can be adjusted on either side of 50 mg. If patient is switched from prednisolone acetate to prednisoloneaurothiomalate, then prednisolone acetate can be used as a starting dosage reference.

A patient on sodiumaurothiomalate therapy will eventually build up gold deposits in most body tissues. Such deposits remain in the tissue for many months or years. Corticoids, on the other hand are excreted in a matter of days or weeks. Since the aforementioned have different excretion patterns, there may be a higher initial and/or maintenance requirement for corticoid.

In certain inflammatory states, in addition to achieving optimal clinical response by switching from one aurothiocorticoid to another, the following method will give dose flexibility within one class of corticoid as follows:

1. Prednisoloneaurothiomalate—50 mg/week
2. Prednisoloneaurothiomalate—50 mg/week Prednisolone acetate—25 mg 3. Prednisoloneaurothiomalate—50 mg/week Prednisolone acetate—50 mg One class of aurothioandrogens of my invention may be illustrated by the following structural formula:

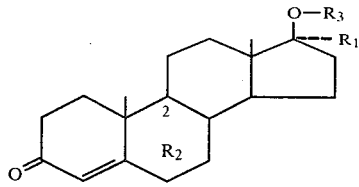

wherein $R_1$ is hydrogen or methyl, $R_2$ is hydrogen or halide and $R_3$ is aurothio moiety, e.g., aurothiomalate.

This class includes 17-aurothio derivates, e.g., 17-aurothiomalate or aurothiogluconate esters of testosterone, methyl testosterone and fluoxymesterone. Another aurothioandrogen is the 3-aurothiomalate of dehydro-iso-androsterone.

Organic aurothio moieties are preferred such as the aurothiomalate and gluconate esters, but inorganic aurothio radicals are also contemplated, e.g., aurothiosulfate radicals. In addition to addition at the 17 position, or 3 position in the case of dehydro-iso-anhdrosterone, the aurothio moiety may be incorporated by addition at other side chain positions or in nuclear configuration or attached to ring carbons.

PREPARATION OF TESTOSTERONE-17-AUROTHIOMALATE

EXAMPLE 7

1 g testosterone is dissolved in 4 cc pyridine, 1 g aurothiomalate anhydride prepared according to Example 1 is added and heated at 100° C. for one hour. Then the contents will be left standing at room temperature for 20 hours. Evaporation of the pyridine and crystallization of the residue from acetone-hexane will give the 17-aurothiomalate of testosterone, as represented by the following structural formula. The aurothio group, which has alpha and beta configurations, is shown in the alpha position:

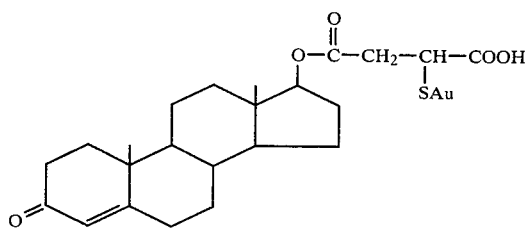

The aurothioandrogen compounds of the present invention possess anti-inflammatory and androgenic activity for the treatment of rheumatoid arthritis and androgen deficiency as well as collagen and autoimmune diseases. They can be administered to provide both androgenic and gold salt therapeutic effects.

Administration of my novel aurothioandrogens eliminates the side effects of corticoid therapy. The novel androgenic-aurothiomalate compounds can be administered for example from about 5–100 mg, or higher, per dosage unit. They may be administered by subcutaneous or intramuscular injection dissolved or suspended in a liquid vehicle. These compounds can also be administered in solid form for subcutaneous implants, suppository, or intra-articular suspension.

The 19-noraurothioanabolics of my invention maybe illustrated by the following structural formula:

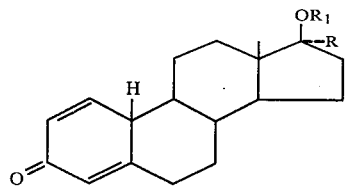

wherein R is hydrogen or methyl and $R_1$ is aurothio moiety.

Organic aurothio moieties are preferred, e.g., aurothiomalate and gluconate esters. This moiety may also be incorporated by steroid addition at other side chain positions or in nuclear configurations or attached to ring carbons.

The 17-beta-aurothioesters are prepared in the same manner as described in Example 7 and are exemplified by delta-1,4-19-nor-androstadiene-3-one-17-alpha-methyl-17-beta-aurothiomalate in which the aurothio radical may be in either the alpha or beta position, with the alpha configuration having the following structural formula:

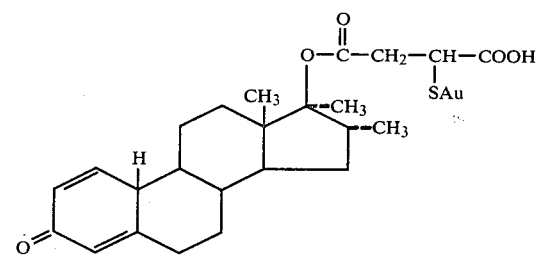

They can be administered to provide both anabolic and gold salt chemotherapeutic effect while eliminating the adverse side effects which accompany corticosteroid therapy.

The novelnoranabolic-aurothiomalate compounds can be administered for example from about 5–100 mg per dosage unit. They may be administered by subcutaneous or intramuscular injection, dissolved or suspended in a liquid vehicle. These compounds can also be administered in solid form for subcutaneous implants, suppository or intra-articular suspension.

The aurothioestrogens of my invention may be illustrated by the following structural formula:

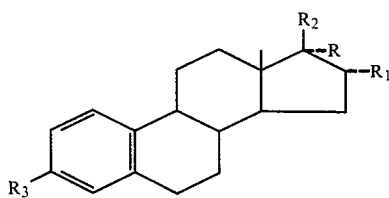

wherein R is hydrogen or ethinyl, $R_1$ is hydrogen, hydroxy or an organic aurothio moiety, $R_2$ is oxo, hydroxy or an organic aurothio moiety, $R_3$ is hydroxy or an organic aurothio radical, e.g., aurothiomalate, with the proviso that at least one of $R_1$, $R_2$ or $R_3$ is an organic aurothio radical.

The class is exemplified by aurothiomalate esters of estrone, estradiol, ethinyl estradiol and estriol.

PREPARATION OF ESTRONE-3-Aurothiomalate

EXAMPLE 8

To a solution of 1 g estrone in 5 cc pyridine is added 1 g of aurothiomalic anhydride prepared according to Example 2 and the contents warmed to 70° C. for 30 minutes and then left standing at room temperature overnight. Removal of pyridine under vacuum and crystallization of the residue from acetone-hexane yields 3-aurothiomalate (alpha and beta) of estrone which, in its alpha configuration is represented by the following structural formula:

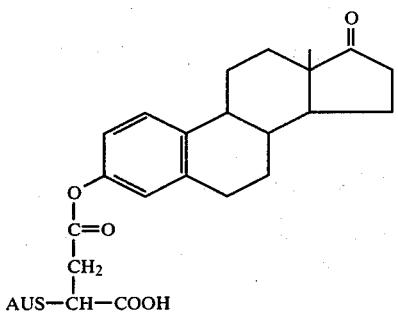

Also included in the present invention is the 17-beta-aurothio ester of ethinyl estradiol. The aurothiomalate ester moiety is preferred, but other organic aurothio esters may be used, e.g., the aurothiogluconate and this moiety, which may also be inorganic, e.g., thiosulfate, may be incorporated by steroid addition at other side chain positions or in a nuclear or attached ring position.

An example of a diaurothioestratriene is delta-1,3,5(10)-estratriene-3,17-beta-diaurothiomalate. In the following structural formula the aurothio radical is depicted in the alpha position, but it also exists in the beta position:

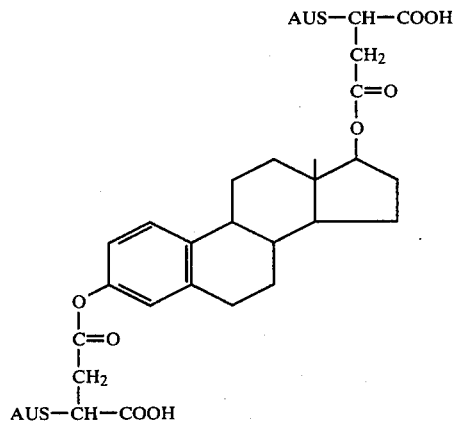

An example of triaurothiomalate is delta-1,3,5(10)-estratriene-3,16,17-triaurothiomalate:

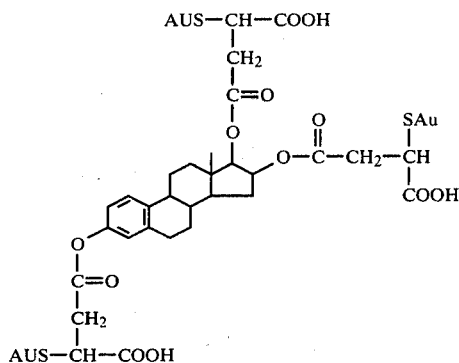

The aurothio groups can be in either the alpha or beta position.

The aurothiomalate-estrogenic compounds of the present invention possess anti-inflammatory and estrogenic activity for the treatment of rheumatoid arthritis and menopausal and other conditions related to estrogen deficiency, since they can be administered to provide estrogenic and gold chemotherapeutic effects while eliminating the adverse side effects accompanying corticosteroid therapy. The novel aurothioestrogen compounds can be administered orally or by injection in liquid vehicle or solid dosage forms. It should also be noted that, since replacement requirements of estrogen are low, provision can be made for adequate anti-inflammatory response by administering either ethinyl estradiol, estrone, estradiol or estriol. That is, a range of anti-inflammatory dose can be obtained by choice of estrogen compound.

What is claimed is:

1. A compound selected from the group represented by the formula

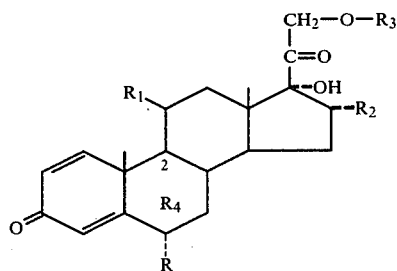

wherein R represents hydrogen, alkyl or halide, $R_1$ represents hydroxy or oxo, $R_2$ represents hydrogen, hydroxy or alkyl, $R_3$ represents an organic aurothio moiety and $R_4$ represents hydrogen or halide.

2. A compound having a formula according to claim 1 in which R represents hydrogen, methyl or flourine, $R_1$ represents hydroxy or oxo, $R_2$ represents hydrogen, methyl or hydroxy, $R_3$ represents aurothiomalate and $R_4$ represents hydrogen or fluorine.

3. A compound selected from the group represented by the formula

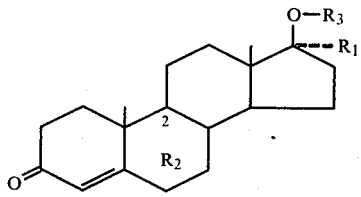

wherein $R_1$ represents hydrogen or methyl, $R_2$ represents hydrogen or halide and $R_3$ represents an organic aurothio moiety.

4. A compound having the formula according to claim 3, wherein $R_1$ represents hydrogen or methyl, $R_2$ represents hydrogen or halide and $R_3$ represents aurothiomalate.

5. A compound selected from the group represented by the formula

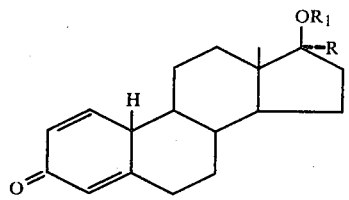

wherein R represents hydrogen or alkyl and $R_1$ represents an organic aurothio moiety.

6. A compound having the formula according to claim 5, wherein R represents hydrogen or methyl and $R_1$ represents aurothiomalate.

7. A compound selected from the group represented by the formula

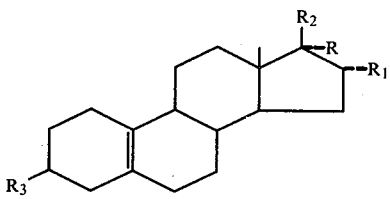

wherein R represents hydrogen or ethinyl, $R_1$ represents hydrogen, oxo, hydroxy or aurothio moiety, $R_2$ represents hydrogen, oxo, hydroxy or aurothio moiety and $R_3$ represents hydrogen, oxo, hydroxy or aurothio moiety.

8. A compound having the formula according to claim 7, wherein R and $R_1$ represent hydrogen, $R_2$ represents oxo and $R_3$ represents aurothiomalate.

* * * * *